(12) United States Patent
Batal et al.

(10) Patent No.: US 12,030,030 B1
(45) Date of Patent: Jul. 9, 2024

(54) MODULAR SYNTHESIZER ASSEMBLY

(71) Applicant: NITTO DENKO AVECIA INC., Milford, MA (US)

(72) Inventors: John Batal, Milford, MA (US); Matthew Pelletier, Arlington, MA (US)

(73) Assignee: Nitto Denko Avecia, Inc., Milford, MA (US)

( * ) Notice: Subject to any disclaimer, the term of this patent is extended or adjusted under 35 U.S.C. 154(b) by 253 days.

(21) Appl. No.: 17/169,424

(22) Filed: Feb. 6, 2021

Related U.S. Application Data

(60) Provisional application No. 62/975,619, filed on Feb. 12, 2020.

(51) Int. Cl.
*B01J 19/24* (2006.01)
*C07H 1/00* (2006.01)
*C07H 21/00* (2006.01)

(52) U.S. Cl.
CPC ............. *B01J 19/245* (2013.01); *C07H 1/00* (2013.01); *C07H 21/00* (2013.01); *B01J 2219/0004* (2013.01); *B01J 2219/00871* (2013.01)

(58) Field of Classification Search
CPC . B01J 19/00; B01J 19/24; B01J 19/245; B01J 2219/00; B01J 2219/00002; B01J 2219/00027; B01J 2219/0004; B01J 2219/00781; B01J 2219/00581; B01J 2219/00871; C07H 1/00; C07H 21/00
See application file for complete search history.

(56) References Cited

U.S. PATENT DOCUMENTS

| | | | |
|---|---|---|---|
| 5,641,459 A | 6/1997 | Holmberg | |
| 5,807,525 A * | 9/1998 | Allen | B01J 19/0046 422/62 |
| 2006/0280651 A1* | 12/2006 | Bellafiore | B01J 19/0046 422/62 |
| 2011/0021749 A1* | 1/2011 | Demmitt | B01J 19/0046 536/25.3 |

* cited by examiner

*Primary Examiner* — Natasha E Young
(74) *Attorney, Agent, or Firm* — Lippes Mathias LLP

(57) ABSTRACT

A system for synthesizing organic polymers utilizing one or more independent synthesizer elements of similar design configured to interconnect to one another for combined operations. The synthesizer module contains at least two small-cavity pumps in a symmetric valve and tubing arrangement for delivery, blending and/or recirculation of synthesis reagents. The synthesizer module allows it to operate independently to perform synthesis chemistry, or two or more modules can be combined.

19 Claims, 10 Drawing Sheets

Conditions of Coupling

| No. | 1 | 2-1 | 2-2 | 3-1 | 3-2 | 4-1 | 4-2 | 5-1 | 5-2 |
|---|---|---|---|---|---|---|---|---|---|
| Synthesizer | First | First | Second | First | Second | First | Second | First | Second |
| Procedure of synthesis | control | See Procedure2 | | See Procedure3 | | See Procedure4 | | See Procedure5 | |
| Equivalent of amidite | 1.3eq | 1.0+0.6eq | 1.0eq | 1.0+0.6eq | 1.0eq | 1.6eq | 1.0eq | 1.6eq | 1.0eq |
| Pushing ACN for transfer solution | - | 2.5CV (16ml) | - | 2.5CV (16ml) | - | 2.5CV (16ml) | - | 2.5CV (16ml) | - |
| ACN Washing volume of transfer tube | - | 0 | - | 2CV (12ml) | - | 2CV (12ml) | - | 2CV (12ml) | - |
| Switching valves when washing transfer tube | - | No | No | No | No | No | No | Yes | Yes |

FIG. 9

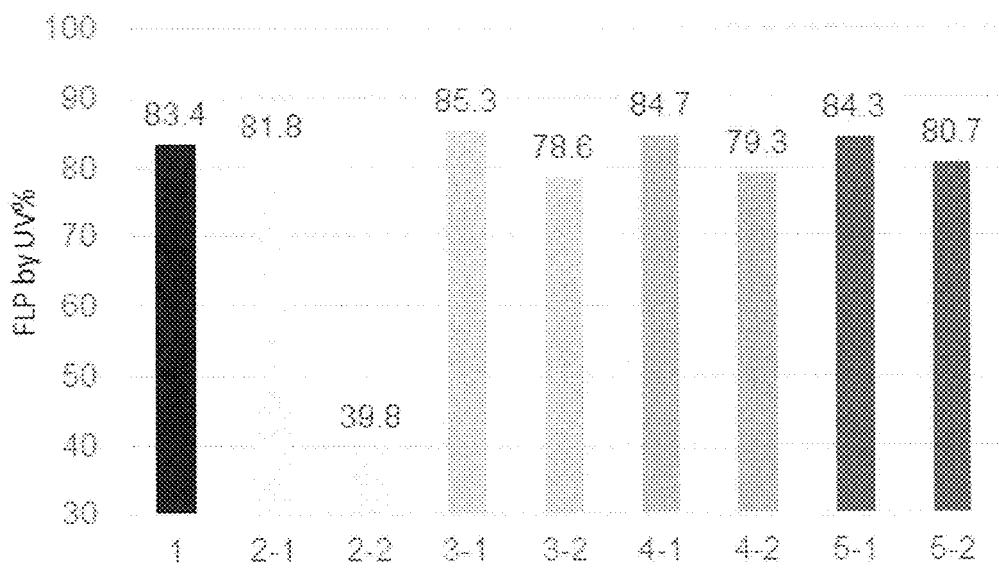

FIG. 10

MODULAR SYNTHESIZER ASSEMBLY

This application claims the benefit of U.S. Provisional Application Ser. No. 62/975,619, filed Feb. 12, 2020, the disclosure of which is herein incorporated by reference.

BACKGROUND

The present exemplary embodiment relates to systems and methods for synthesizing molecules. The present embodiments relate to a device and method for synthesizing biological polymers such as polypeptides and oligonucleotides. More specifically, the disclosure is directed to a solid-phase synthesizer system whose design is modular to provide a virtually unlimited range of commercial scale operation using minimal hardware. However, it is to be appreciated that the exemplary embodiment is also amenable to other similar applications.

An oligonucleotide is a macromolecule comprising a sequence of nucleosides, each of which includes a sugar and a base. Each nucleoside is separated from adjacent nucleosides with an internucleosidic linkage, which effectively serves to bond the nucleosides together. The sugar can be a pentose, such as a deoxyribose, ribose, or a derivative of pentose. A number of different bases and substituted bases can be used, the four most common of which are adenine, cytosine, guanine, and thymine (abbreviated as A, C, G, and T, respectively). The internucleosidic linkage is most commonly a phosphate, which may be substituted with a variety of substituents at a nonbridging oxygen atom, most commonly by sulphur or an alkyl, ester, or amide group.

Oligonucleotides are among the most important and prevalent reagents used in biotechnology laboratories engaged in research, diagnostics and therapeutics. The high demand for oligonucleotides derives from their specificity for complementary nucleotide sequences in DNA or RNA. Different methods are used for synthesizing oligonucleotides, including phosphoramidite, phosphotriester, and H-phosphonate methods, each of which is generally known in the field of biochemistry.

Solid-phase based, multi-stage synthesis of complex organic molecules using controlled fluid flow across a fixed bed is one accepted methodology of nucleic acid synthesis. This general technique has been successfully applied to the synthesis of peptides, oligonucleotides and similar long-chained organic substances. A comprehensive discussion of the chemistry, synthesis techniques, and equipment currently used for oligonucleotide production appears in "Manufacturing of Oligonucleotides", E. Paredes, V. Aduda, KL. Ackley, and H. Cramer, Comprehensive Medical Chemistry, $3^{rd}$ Edition, 2017 Elsevier Inc., herein incorporated by reference.

Commercial-scale production of a growing variety of oligonucleotides has become increasingly important as these substances have moved out of the laboratory and into mainstream therapeutic applications. Commercially available oligonucleotides are typically at least 4 nucleotides in length, with 15 to 30 nucleotides being the most common length.

In one system for producing oligonucleotide molecules, a solid support can be provided in a reaction vessel and a large number of protected nucleosides can be affixed to the solid support. A deprotectant, acting through a detritylation mechanism, is added to remove the most widely used DMT protecting group from the nucleoside, and thus to "deprotect" a hydroxyl group. As a result, the last residues in the sequence have hydroxyl groups that are ready to receive a next amidite. Nucleoside phosphoramidites (hereafter also referred to as "amidites"), dissolved in a solvent such as acetonitrile (ACN), are introduced into the vessel. An activator can also be introduced into the vessel with the amidites. The phosphorus in the amidites bonds with the oxygen in the hydroxyl, thus providing support-bound nucleotides. After the support-bound nucleotides are formed, excess amidites can be flushed from the vessel with ACN. An oxidizing agent can then be added to convert the trivalent phosphite to pentavalent phosphate. After the oxidizing agent is flushed, a capping agent can be added to block the unprotected hydroxyls from reacting with amidites introduced at a later stage. ACN can again be introduced to flush out the capping agent. These steps can be repeated a number of times to produce growing, oligonucleotide chains from support-bound nucleosides.

Traditional solid-phase synthesizers use inter-connected tubing, pumps, and valves to control the flow and mixing ratio of various washing fluids and reaction solutions. A synthesizer is essentially a metering system which blends and delivers the synthesis reagents to a connected reaction vessel. The reaction vessel for synthesis is a separate device, which is typically a cylindrical packed bed of solid support. In many embodiments, the reaction vessel may be a column. The synthesizer delivers a series of solution doses to the reaction vessel, with each dose displacing the previously introduced solution. Some solutions are additionally recirculated through the reaction vessel in order to complete reactions which require extended contact time.

The reaction cycle succession is controlled by a synthesis method or recipe that guides the delivery of reagents in the requisite order for the oligonucleotide being synthesized. Thus, the sequence of reactions for a plurality of oligonucleotides is performed in order such that detritylation is carried out for each oligonucleotide, then coupling is carried out for each oligonucleotide, followed by capping of each oligonucleotide followed by oxidation of each oligonucleotide. The cycle is then repeated until full length oligonucleotides are obtained.

In commercial scale batch manufacturing, the daily synthesis capacity is limited by the range of scale of purchased equipment. Increasing or decreasing the capacity will require a much larger or a much smaller unit, which adds cost, complexity, and dissimilarity of design between scales. A modular design provides a virtually unlimited manufacturing scale range using the same process design and equipment elements. It also provides utility for additional raw material optimization with increasing scale, which is further described in the embodiments.

A prior art synthesizer apparatus is shown in FIG. 1. Reaction vessel 88 is first loaded with a suitable starting material, such as a protected nucleoside or other building blocks, fixed at one end of the chain to a suitable polymeric support or other alternatives such as Controlled Pore Glass (CPG) beads. Reaction vessel 88 is then connected to a set of reagent reservoirs by an interconnected system of fluid conduits (not numbered). A suitable deblocking compound, such as a solution of dichloro acetic acid (DCA) in methylene chloride, is then withdrawn from fluid reservoir 144 through three-way valves 126 and 128 and routed through the fluid conduit containing pump 80, flowmeter 82, and one or more valves, such as three-way valves 86 and 87, to the bottom of reaction vessel 88. The deblocking solution is then passed upward through vessel 88 contacting the protected nucleoside or oligonucleotide fixed to the CPG beads resulting in unblocking or activating those functional groups. A flow stream comprising reaction by-products and excess deblocking solution is withdrawn as effluent from the top of vessel 88, passed through one or more control valves, such as three-way valves 90 and 91, and directed through or past a monitoring device, such as optical scanner 92, which continuously monitors the chemical composition of the flow stream exiting vessel 88 via communication with computer 100.

During at least some of the process steps, it may be desirable to recycle some portion of the reactor effluent as recycle stream 95 coming out of three-way valve 94, mixing stream 95 with fresh reagent at three-way valve 79, while withdrawing another portion of the effluent as waste stream 96 for disposal. A moisture monitoring device 77 can monitor moisture levels in both the fresh reagent and the recycle stream.

Upon completion of the deblocking step, valve 126 is closed to stop the flow of deblocking solution from reservoir 144. Instead, two-way valve 110 and three-way valves 112, 114, 122, 124, 126 and 128 are positioned to permit the flow of washing fluid, typically acetonitrile, from wash reservoir 20 through the connecting fluid passage to the bottom of vessel 88. Along the way to vessel 88, the wash fluid would flush the fluid passageway of residual deblocking solution. As the wash fluid passes through the interior of vessel 88, it also picks up residual deblocking solution and by-products of the deblocking reaction.

Upon completion of this wash step, it is time to begin reaction step 2 of the cycle, the coupling step. Valves 110 and 128 are closed to stop the flow of acetonitrile wash fluid, and, instead, valves associated with one of the several amidite reservoirs are opened. Reservoirs 30, 32, 34, 36, 38, 40, 42 and 44 hold eight different amidites which can be used in the synthesis of a desired oligonucleotide. It will be apparent to those skilled in the art that fewer or greater numbers of amidite reservoirs may be utilized in this system as required for a particular synthesis. Each amidite reservoir has associated therewith a three-way valve, namely valves 50, 52, 54, 56, 58, 60, 62 and 64 respectively.

Activator compound is stored in reservoir 72 and is also fed into the system during the coupling step 2 via three-way valve 74 and pump 76. The flow meter 68 monitors the different stream flowrates. These flowrates are utilized by the process controller 100 to adjust the pumps 80 and 76 to provide activator and amidite through the three-way mixing valve 70 to the reaction chamber 88. Another monitoring device 78 may be used to confirm the identity of the amidite being added. Similarly, optical scanner 84 may path monitor the composition of the feed stream. Two-way valves 22 or 24 could be positioned to facilitate flushing that line with wash fluid.

Upon completion of this second wash step, it is time to begin oxidation step 3. Valves are closed to stop the flow of wash fluid, and, instead, three-way valves 124, 126 and 128 are opened to begin the flow of oxidizing or sulfurizing solution from oxidation reservoir 142.

Upon completion of a third wash step, it is time to begin capping step 4. Two-way valves 132 and/or 140, together with valves 122, 124, 126 and 128, are positioned to begin the flow of capping compound to vessel 88. A ratioed mixture of two different capping compounds may be utilized in this step. As illustrated, reservoir 130 contains a first capping material, such as acetic anhydride, while reservoir 138 contains a second capping material, such as a base N-methyl imidazole. A suitable feed ratio can be maintained using pump 134 and flowmeter 136. Upon completion of a fourth wash step, a single chain-building cycle is completed.

The system of FIG. 1 suffers from shortcomings such as minimal flexibility in volume, significant waste and imprecision. Moreover, the prior art system is particularly inefficient when used in association with either a proportionally small reaction vessel or proportionally large reaction vessel. Particularly, the system volume associated with a pump attachment with each reagent/reactant reservoir adds volume. When the relative volume of the synthesizer flow rate to the reaction vessel is close, significant waste results when a particularly reaction is completed, and the synthesizer is flushed. The present disclosure describes a method of synthesizing that overcomes limitations which are summarized in Paredes (1) [Paredes et al, Manufacturing of Oligonucleotides, Comprehensive Medicinal Chemistry III, 2017, Pages 233-279].

BRIEF DESCRIPTION

Various details of the present disclosure are hereinafter summarized to provide a basic understanding. This summary is not an extensive overview of the disclosure and is neither intended to identify certain elements of the disclosure, nor to delineate scope thereof. Rather, the primary purpose of this summary is to present some concepts of the disclosure in a simplified form prior to the more detailed description that is presented hereinafter.

According to a first embodiment, a system for synthesizing organic polymers is provided. The system includes one or more synthesizer units (hereinafter alternatively referred to as modules) together with a reaction vessel or vessels (alternatively referred to as a column(s)), designed for interconnectivity to expand scale range, adjust system proportional volumes/flow rate and expand operational complexity. Each module provides liquid monomers and reagents to a fluidly connected reaction vessel. Each module is additionally capable of recirculating liquid displaced from the reaction vessel. A first synthesizer module includes a plurality of monomer inlet ports. Each of the monomer ports can be associated with a different type of monomer. Each monomer port includes an inlet valve for receiving the associated monomer and at least one pump per module to provide blending operations. Each module has a symmetric fluid path of common length to its respective inlet and outlet connections. A controllable inlet valving arrangement fluidly couples to the outlet port of the synthesizer module for providing the selected monomer or reagent to the reaction vessel. A controller controls the pumps, the blending ratio, and the controllable valving arrangement for either delivery or recirculation of solutions. Each module further includes valving for fluid interconnection to another synthesizer module and/or reaction vessel. An optional second synthesizer module is in fluid communication with the first synthesizer module, whose controller acts in programmed modes of coordination with the first synthesizer module.

According to a second embodiment, an apparatus for synthesizing oligonucleotides in a batch process is provided. The apparatus is comprised of one or more independently operating synthesizer units specifically designed for parallelization and is able to deliver an extremely wide process scale range. The unique form of each synthesizer unit provides modularity, so that each unit can operate independently, or two or more units can operate in tandem with cross-communicated and coordinated control.

According to a further embodiment, the system includes one or more individual synthesizer modules whose purpose is to control the flow and mixture ratio of a plurality of reagent solutions. Each module is capable of delivering one or more, preferably at least two reagents, in unison to a reaction vessel. The system can deliver monomers and control the proportions of reagent mixtures to a reaction vessel containing solid-phase support. The system can also recirculate the flow of liquid displaced from the reaction vessel. The system will include at least one synthesizer module, including a plurality of monomer inlet ports, each of the monomer ports associated with one of the different types of monomers. At least two pumps can be provided for the blending and recirculation operations. A controllable inlet valve manifold arrangement is fluidly coupled to an outlet port of the synthesizer module for providing the selected monomer or solution mixture for introduction to the reaction vessel. A controller is provided to control the pumps, the blending ratio, and the controllable valve fluid path arrangement. The module includes further valve connection points for fluid communication to another synthesizer module and/or reaction vessel. A second synthesizer module can be provided in fluid communication with the first and/or reaction vessel. A controller of the second synthesizer module can act in programmed modes of coordination with the first synthesizer module.

According to a further embodiment, a method of synthesizing oligonucleotides is provided in which excess reagents are shared among two or more parallel batch reaction vessels. The method uses at least two synthesizer modules capable of independent operation. In an exemplary case involving the coupling reaction of an oligonucleotide synthesis, the modules are operated in sequence wherein a first module provides an activated nucleotide solution to a first reaction vessel at a molar equivalent excess. The un-used excess nucleotide from the first reaction vessel is delivered to the second reaction vessel for the purpose of further consumption and waste reduction, which in this example would otherwise be disposed due to instability after mixing with the associated activator solution. Automated operations within the second reaction vessel are performed independently by the second module which operates in a following mode.

According to another embodiment, an apparatus for the multi-stage solid-phase synthesis of long-chained organic compounds is provided. The apparatus includes a reaction vessel suitable for containing a support material and attached building blocks; a plurality of fluid reservoirs; conduits interconnecting each of the fluid reservoirs with the reaction vessel; valves associated respectively with each of the fluid reservoirs; and gear pumps providing fluid flow through the conduits for provide a feed stream to the reaction vessel. The pumps number less than 4 of the valve means. Optical scanning units monitor ultraviolet or visible light of at least two wavelengths for continuously monitoring the chemical composition of effluent from the reaction vessel.

BRIEF DESCRIPTION OF THE DRAWINGS

The invention consists in the novel parts, construction, arrangements, combinations and improvements, shown and described. The accompanying drawings, which are incorporated in and constitute a part of the specification illustrate one embodiment of the invention and together with the description, serve to explain the principles of the invention.

FIG. 9 is a table outlining the Conditions of Coupling employed in the Examples.

FIG. 10 is graphical depiction of full length of product (FLP) obtained for the Examples.

DETAILED DESCRIPTION

Figure 1:
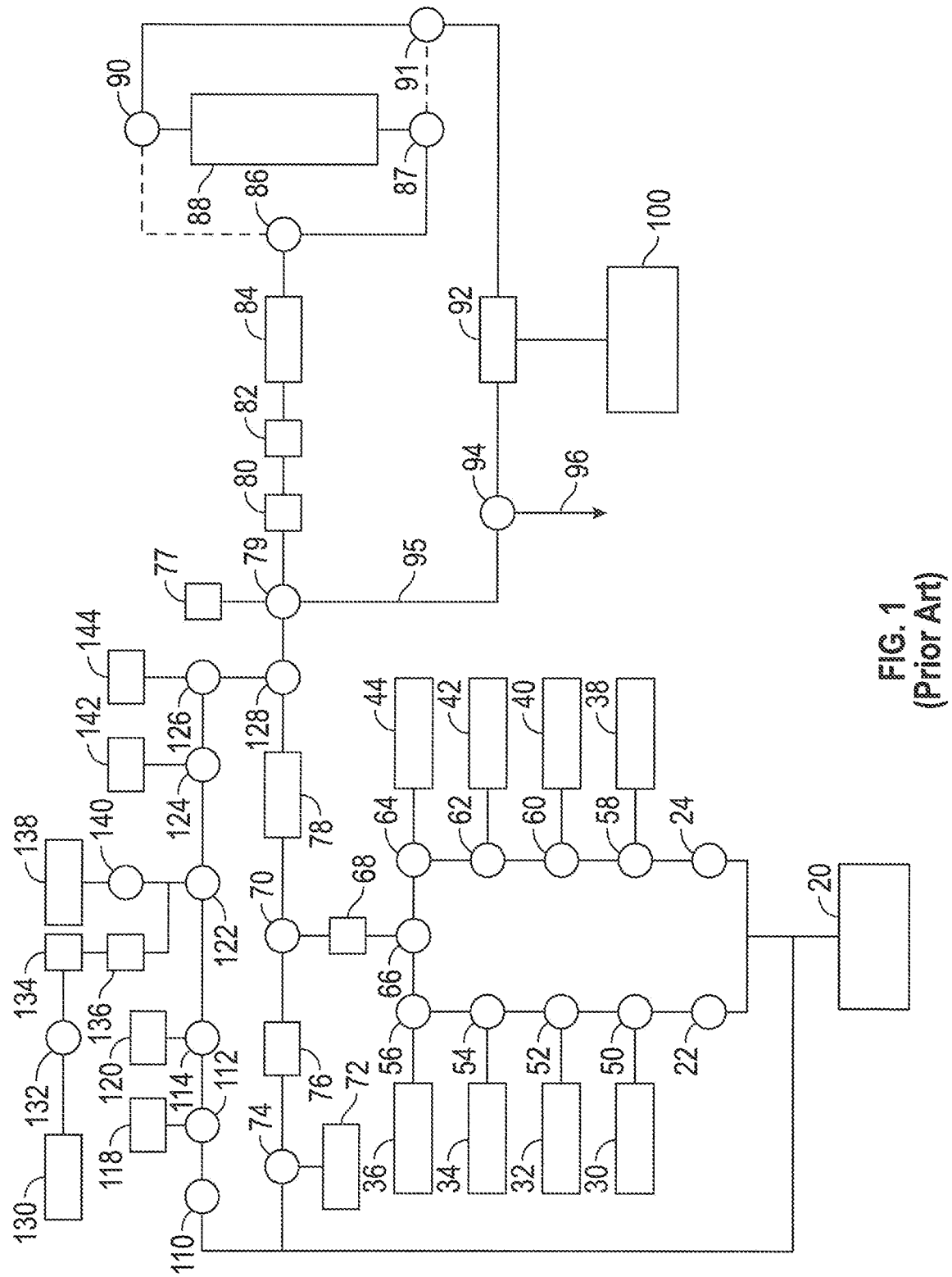
FIG. 1 is a block diagram of a prior art synthesizing apparatus.
Figure 2:
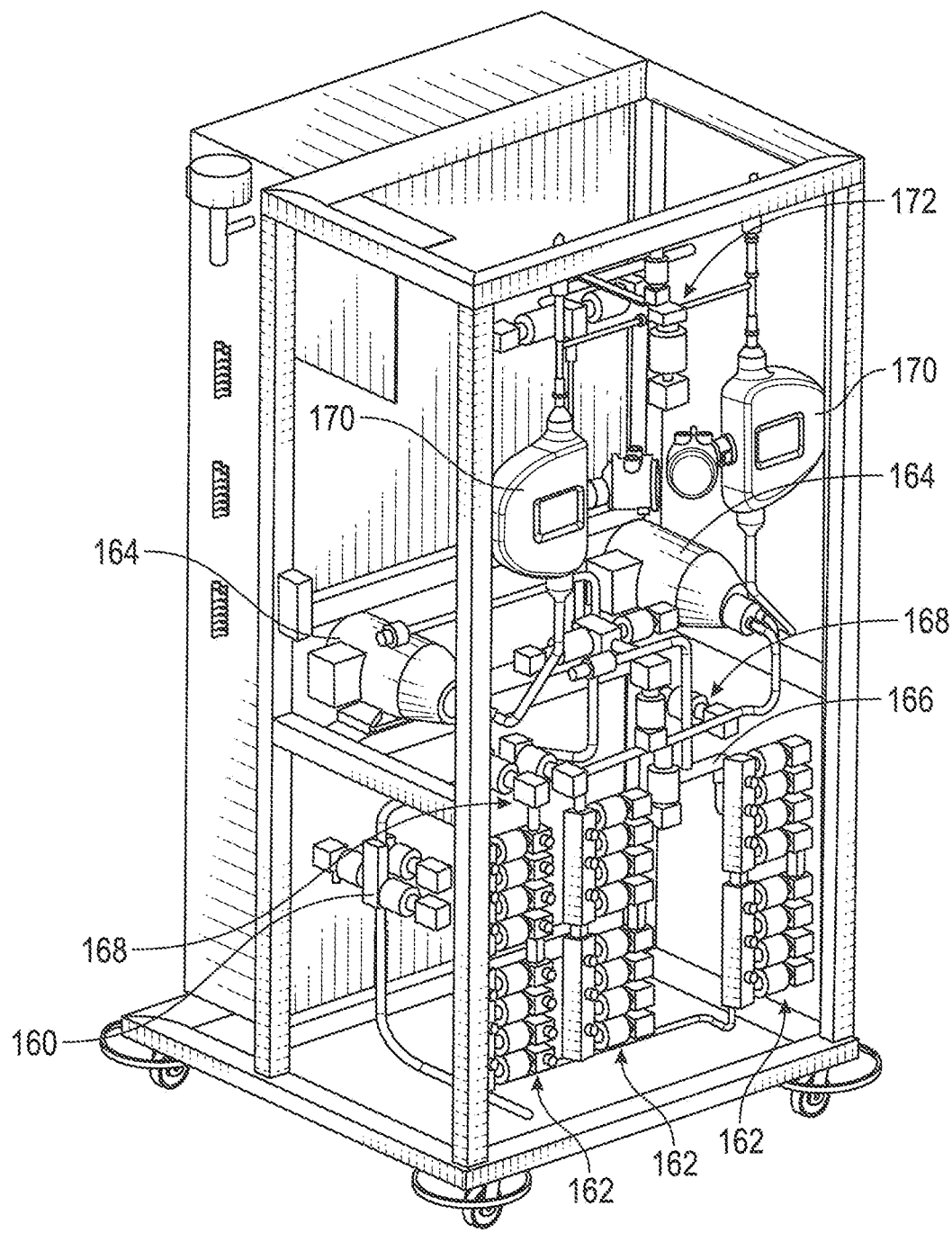
FIG. 2 is a perspective view of a synthesizer module of the present disclosure.
Figure 3:
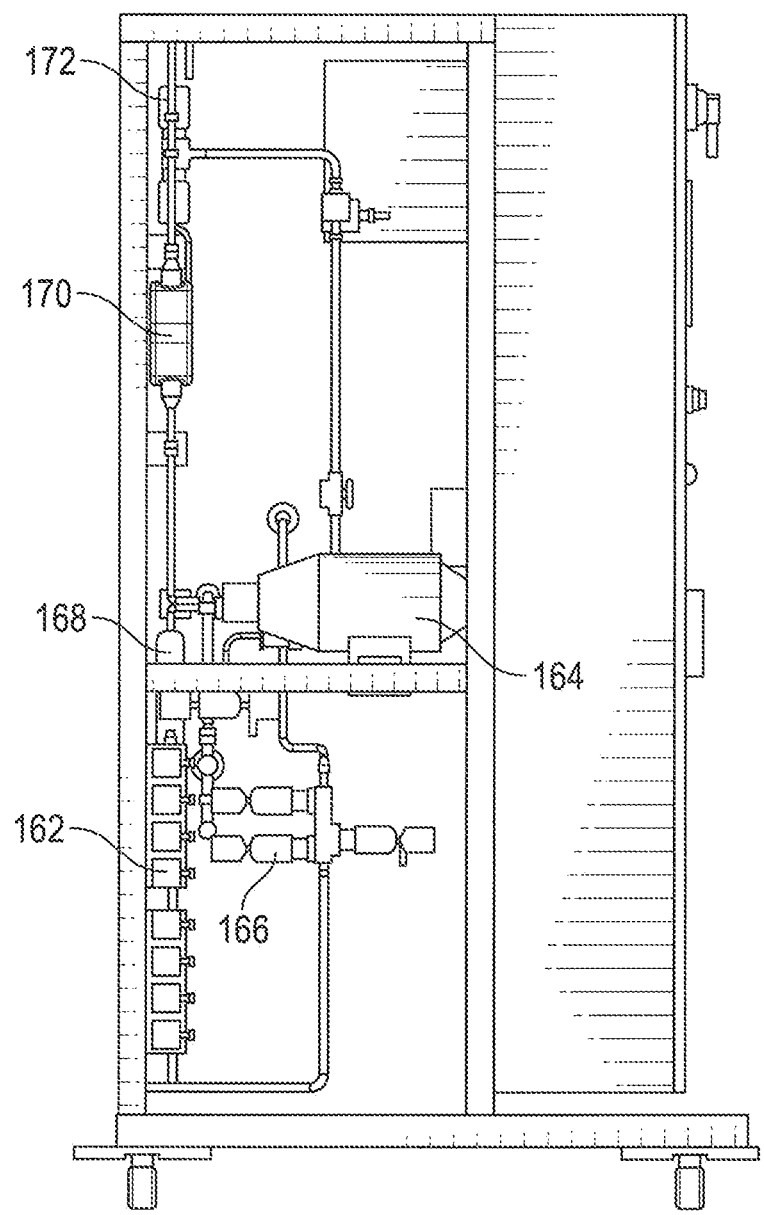
FIG. 3 is a side elevation view of the module of FIG. 2.

Referring now to FIGS. 2 and 3 the synthesizer module is illustrated. The module includes a plurality of regent manifold block valves in red. Each of the valves can feed reagent/solvents to the orange gear pumps that form two symmetrical sides of the synthesizer module. Bulk fluid inlets are shown in blue and similarly feed fluids to the pumps. Green flow valves control feed sequencing to the pumps. Purple flow meters monitor fluid flow to the beige outlet valves which in turn control delivery of fluids to a reaction vessel or an interconnected second synthesizer module.

Each synthesizer module contains two progressive cavity pumps with low internal volume, which are connected using a symmetric piping and valve arrangement capable of delivering at least two reagents in unison to a reaction vessel. In this arrangement, the reagent solutions have a flowpath of common length and are kept as short as practical. This ensures that the mixture proportions can be maintained during simultaneous delivery of reagents, since the inlet connection point of each reagent is the same distance from the reaction vessel inlet. As such, the internal dilution volumes are kept to a minimum, and reactants will not reach the reaction vessel at disparate times or reduce chemical precision due to either timing of delivery, or by dilution which may occur during recirculated flow operations.

The present synthesizer module employs minimal hardware elements (pumps and valves) resulting in lower cost and a smaller footprint, while providing an exceptionally wide flow range, e.g. 0.25 to 38 lpm, through the connected reaction vessel (or a "turndown" of more than 150:1) on a large range of reaction vessels, e.g. 15 cm to 80 cm in diameter. Using currently available high-loaded oligonucleotide support (e.g. NittoHL), this equates to a range of scales from 50 mmol to 1600 mmol, or a manufacturing scale range of 32:1, in the same production time using a single synthesizer module. By adding additional modules, the capacity can be doubled by adding a second module, or tripled by adding a third module, etc. when commonly connected to increasingly larger reaction vessels, or by using other modular operation strategies further discussed in the embodiments.

Figure 4A:
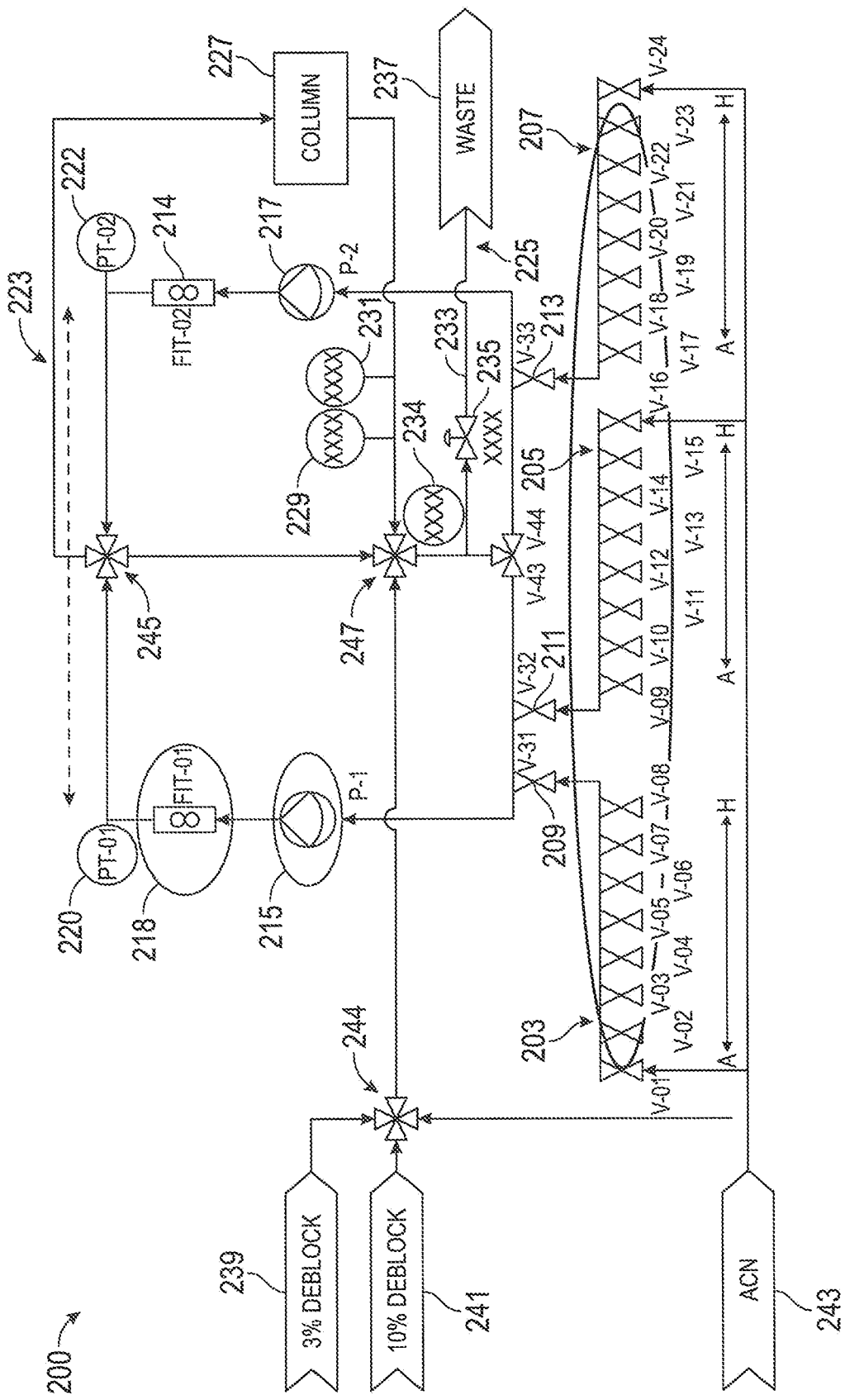
FIG. 4A is a block diagram of the synthesizer of the present disclosure.
Figure 4B:
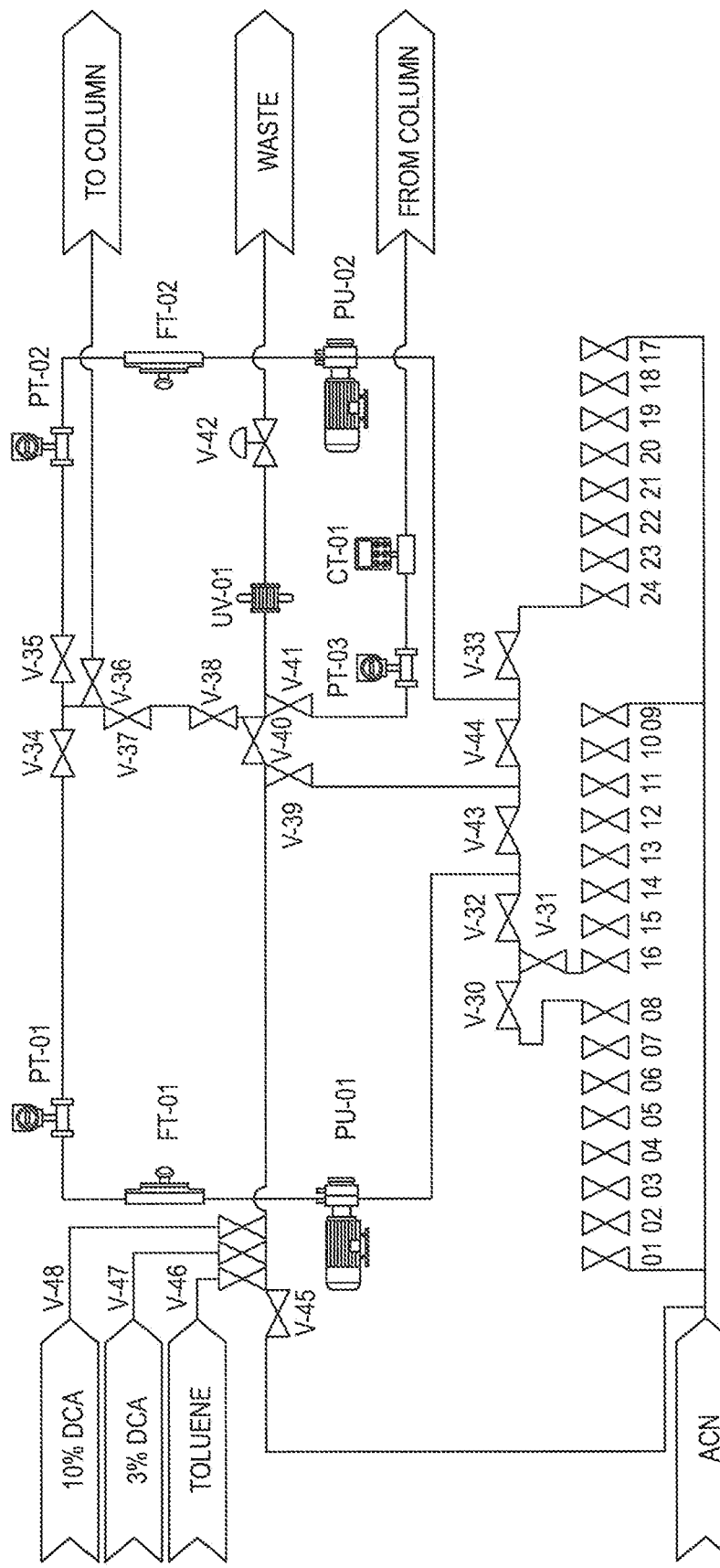
FIG. 4B is a block diagram of a slightly modified synthesizer configuration.

With reference to FIG. 4A, a schematic illustration of the present system is depicted. The system 200 includes a plurality of manifold valves A-H in blocks 203, 205 and 207. Each of blocks 203, 205 and 207 feed reagent/solvents to valves 209, 211 and 213, which in turn are in fluid communication with gear pumps 215 and 217 forming symmetrical sides of the synthesizer (modules). Each valve A-H is in fluid communication with a reagent reservoir (not shown). Each pump includes an associated flow meter 218 and 219 which is in fluid communication with reaction vessel loop 223 and discharge path 225. A program relief mechanism 220/222 is provided with each pump side. Reaction vessel loop 223 includes reaction vessel 227 and optical sensors 229 and 231. Discharge loop 225 feeds outlet line 233 including optical sensor 234 and control valve 235 which lead to waste receptacle 237. 3% deblock is received from storage element 239 and 10% deblock from storage element 241. Acetonitrile is received from storage element 243. Four way valve 244 controls the reagent. Four way valve 245 and 247 control each of the reaction vessel loop 223 and discharge loop 225. The present system benefits by elimination of a separate recirculation piping loop. FIG. 4B illustrates how the flow configuration of FIG. 4A can be arranged when block-style diaphragm pumps are employed.

The synthesizer module of FIGS. 4A and 4B provides for recycling through the reaction vessel, and delivery of bulk reagents such as oligonucleotides, deblock solution and acetonitrile at much higher flow rates by employing the same pumps in a parallel fashion. It also eliminates unswept fluid contact areas or "dead legs". Furthermore, the synthesizer module eliminates a separate recirculation loop which would otherwise require flushing after recirculation operations. This allows the piping to be cleared of residual reagents between each synthesis step using the same fluid which is already used to wash the reaction vessel. In doing so, the amount of waste from synthesis is reduced and the efficiency of reagent clearance is improved for a positive impact on product purity.

Each module can include feed ports; one dedicated reaction vessel return; one dedicated feed from other modules; one dedicated 3% deblock feed; one dedicated 10% deblock feed; one dedicated reaction vessel feed/other module return; one dedicated toluene feed; one dedicated waste outlet; and one dedicated reaction vessel outlet. Preferably, only two pumps will be employed. Air actuated multi-port integrated block diaphragm valves can be used to minimize the length of flow paths with an air actuated pinch valve to control system backpressure at the waste outlet.

Metal product contact surfaces can be constructed from 316/316L stainless steel or Hastelloy with surfaces electropolished or chemically passivated, and a polished surface finish for very efficient rinse clearance. The preferred product contact elastomeric materials are PTFE (Teflon), FFKM (Kalrez), and PEEK for chemical resistance. PTFE-lined braided hose can be used for process interconnections and to relieve strain or reduce vibration. Lines can be sloped to maximize free draining of materials and to eliminate air accumulation in flow meters and other instruments.

The pumps can be designed to magnetically de-couple from the drive in the event of dead head operation to prevent over-pressurization and with secondary protection provided by software safety interlock.

The present system is advantageous in that the employed gear pump (as opposed to the traditional multi-head diaphragm pump with associated tube manifold) is of exceptionally low volume. As such, the pumps can be cleared of residual reagents using only the amount of wash solvent which was already required to wash the reaction vessel between steps. This reduces the cost of manufacture by eliminating waste and minimizing the environmental footprint. Functionally, the gear pump delivers near square wave flow response (immediate ramp up/ramp down), which both minimizes waste and maximizes control aligned with the intended recipe parameter conditions. The flow response is immediate and not dependent on flow feedback.

The valves can be diaphragm block valves drilled from stainless steel to minimize internal volume and therefore waste and dilution volume.

The modular design allows for alternative modes of operation, such as performing multiple simultaneous batches with staged operation. For example, it is envisioned that the modular approach may be employed to re-use excess amidite from coupling via cross-communication with another module to consume the excess in a second reaction vessel. This approach was demonstrated to produce at least a 19% savings of amidite and activator raw materials for a process which uses a 1.6 molar excess of amidite. By extension, a process with 2.5 molar excess has potential for a 30% savings.

Modularity at the software level is achieved by providing independent control within the machine, with provision for cross-coordination with additional units. Each module can contain an embedded or external controller which can independently perform the complete synthesis chemistry process instructions and parameters (hereinafter "recipe") when the module is connected to the inlet and outlet of a reaction vessel. Each controller will additionally synchronize and coordinate operations with other connected controllers of additional modules as they perform parallel or sequentially triggered operations.

Each module can be capable of connecting to another unit for the purpose of common fluid transfer. Each module contains a controller which can operate the module independently to perform a synthesis recipe. The controllers are programmed to synchronize with one or more additional modules to coordinate simultaneous or sequential functions. The benefits of "duplex" or "multi-plex" operation are described in further embodiments.

Each synthesizer module can include pressurized solvent and reagent delivery tanks; a PLC based control system capable of running automated process recipes and communicating with a human machine interface ("HMI") for oversight by operators; reaction vessels; and a liquid handling system with multiple entry points for amidites plus complimentary ports for each of the following: activator solution; acetonitrile; a first detritylation solution; a second different detritylation solution; capping solution A (Cap A); capping solution B (Cap B); oxidation solution; thiolation solution; amines; and toluene. The system can operate in a temperature range of −20-60° C. at a relative humidity of 5-90% RH. Each module can have a physical E-Stop mechanism designed to stop all physical movement of the equipment immediately. The E-Stop mechanism(s) can be located in easily accessible areas on the equipment. This mechanism will also be able to be actuated by the software interface.

The computer control system can include two HMIs. One can be embedded machine-grade interface with the primary purpose of stand-alone operation and on-board data collection. The other can be a secondary remote workstation or SCADA connection for plant wide operator control and enterprise system integration. The primary system control hardware can reside within the main electrical panel on each module. The primary controls and graphical interface can be displayed on a panel-mounted touchscreen machine-grade embedded control interface.

Each module contains a PLC which can independently perform all synthesis operations and can have sufficient I/O for all system instrumentation and control devices. The PLC contains all the necessary logic to independently perform the recipe parameters which are downloaded for synthesis but can also operate in various dependent modes when linked to other modules.

When running in duplex mode (two synthesizers combined) or multi-plex mode, a separate HMI application can be used on a lead machine. The lead machine is the machine on which the recipe is loaded and controlled. Shared variable communication can be used for PLC to PLC communications between the two synthesizer modules. The logic in the PLC allows either synthesizer to become a recipe lead or a follow module.

Figure 5:
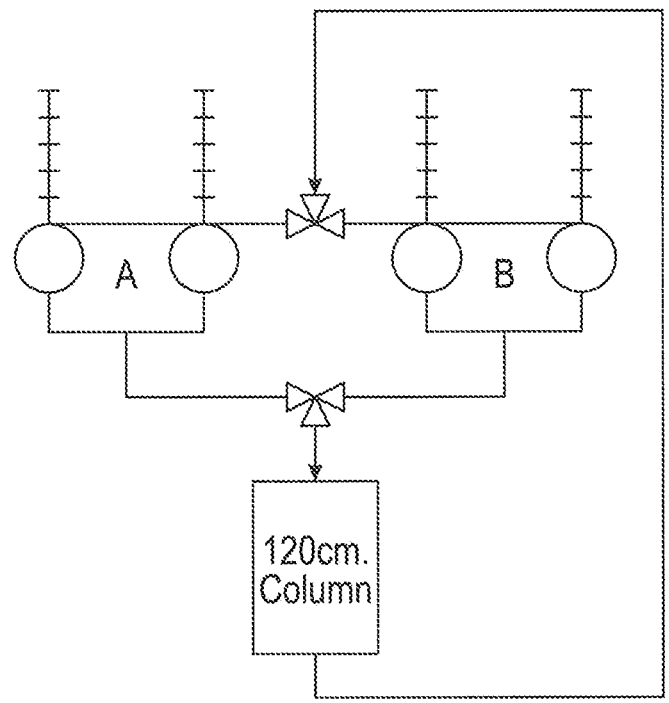
FIG. 5 is a schematic illustration of a dual synthesizer configuration wherein both modules feed a single reaction vessel.

The provisions for duplex or multiplex batch operation in the modular design allows for an increase in both batch capacity and material efficiency. This mode of operation is shown in FIG. 5. More particularly, the system comprises synthesizer modules A and B interconnected via a valving structure to cooperatively feed liquids to the 120 cm. reaction vessel and receive recirculated effluent therefrom.

The tubing, valve and piping arrangement along with the integrated software recipe approach are supported by the controller architecture to anticipate continuity between modules and the coordination of fluid transfer when two or more modules are inter-connected.

The lead/follow relationship between independent module controllers provides the necessary synchronization of batch steps to allow the timely transfer of excess coupling solution from one reaction vessel to the next.

When combining operations in the fashion shown in FIG. 5, the connected modules are able to further multiply the manufacturing scale range. In the currently established chemistry of oligonucleotide synthesis on solid support, certain reactions are conducted with a significant stoichiometric excess of reagent, such as the phosphoramidites used in coupling for oligonucleotides. This has been commonly shown as necessary to drive coupling efficiency to above 99%. Advantageously, the present synthesizer modules being operated in duplex or multi-plex mode allows excess amidite (or "waste") from one reaction vessel to be at least partially consumed to good effect in a second reaction vessel. Similar economy is likely possible for other synthesis reagents, depending on their individual cost and magnitude of excess.

With continuing reference to FIG. 5, the modular design of the synthesizer also allows a single reaction vessel to be connected to two or more synthesizers. In this mode of operation, the supported reaction vessel size can be further increased and thus further widening the range of scale. For reaction vessel sizes between 15 cm and 80 cm, for example, a single module can deliver/recirculate reagents or wash solvents using solution flow rates from 0.25 to 38 LPM. This supports batch sizes from 30 mmol to 1800 mmol based on currently used synthesis media and chemistry limitations on bed height.

To illustrate the effect of this mode of operation, when a second module is connected for use with a single reaction vessel as shown in FIG. 5, the production scale may be doubled by supporting a reaction vessel size greater than 1 meter. The two synthesizer modules could be utilized to (i) work cooperatively to provide a very high volume of reagent(s) to a single reaction vessel; (ii) work cooperatively to provide different reagents simultaneously to a single reaction vessel; or (iii) work together to sequentially feed reagent to a first and then to a second (or more) reaction vessel. For washes, detritylation, and recirculation at higher flows, both pumps can be used to increase the flow range. The use of both pumps is determined by the flow rate and type of solvent. This type of system can also have multiple synthesis beds wherein the units work together to form products including two or more strands because two separate reagents can be delivered to a common bed.

Figure 6:
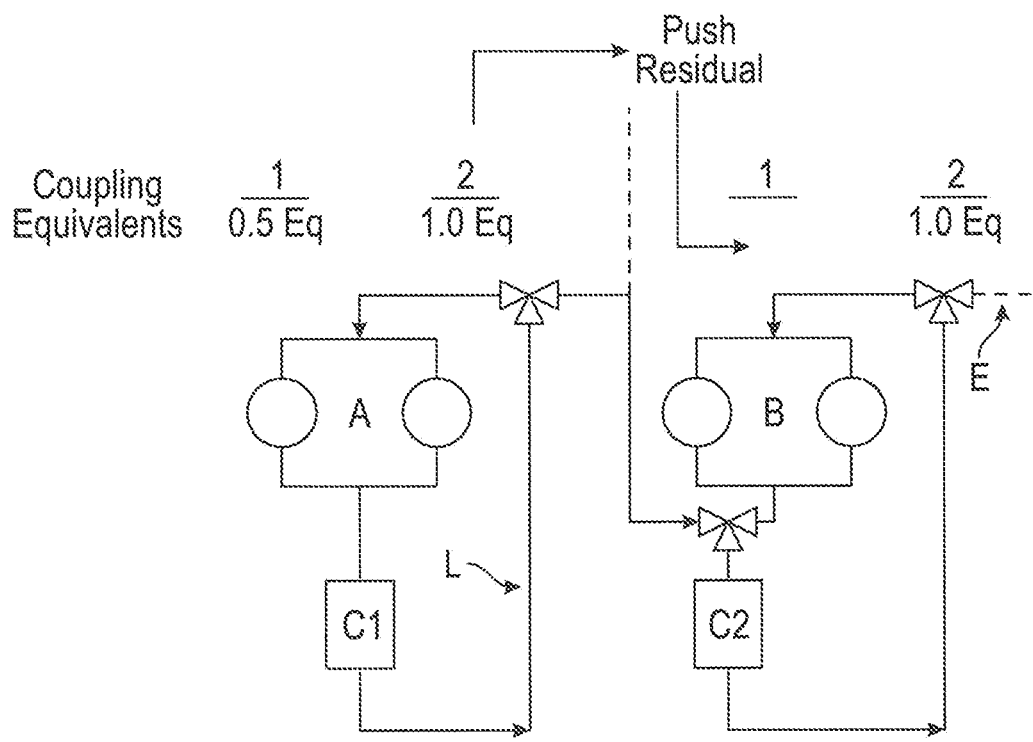
FIG. 6 is a schematic illustration of a dual synthesizer configuration wherein the modules sequentially feed two reaction vessels.

Referring now to FIG. 6, an alternative schematic illustration of the system is provided. A first synthesizer module A is in fluid communication with first reaction vessel C1. A second synthesizer module B is in fluid communication with second reaction vessel C2. Second synthesizer B receives the reaction residue from reaction vessel C1 via line L. Second synthesizer B further receives fresh amidite/coupling activator from an external source E. In this configuration, excess amidite or other reagent can be supplied to reaction vessel C1 via first synthesizer Module A with excess being delivered to reaction vessel C2. Reaction vessel C2 can further receive a suitable amidite or other reagent dosage from synthesizer B. This method of pushing excess amidite has been found to reduce the overall usage.

In short, the unreacted reagent equivalents from the first reaction vessel can be fed to a second module to react with a second reaction vessel. Upon completion of the residual equivalents, a second dose of an additional equivalent can be added. In this manner, waste can be reduced 50%. If this process were performed on four reaction vessels, waste can be reduced to ¼.

In either of the duplex synthesizing module configurations shown, upon power up, each synthesizer module can be independent. If a batch is not in progress, both synthesizers can determine the other's activity mode. If one synthesizer determines that the other is a recipe lead, then it sets itself into follow mode. Each synthesizer can communicate all required values to the other. The recipe engine can include a plurality of synthesis steps which execute sequentially and repeat for the number of cycles (base couplings) used in synthesis, up to 100 cycles, for example.

In stand-alone mode, each synthesizer operates independently. Each machine has a separate HMI application for stand-alone mode, and a recipe is loaded on each machine to perform two separate batches which can be run simultaneously, for two separate batches of any sequences.

HMI software can control access to the system, including manual and automatic operation, maintenance, data historian, recipe writing/storage, and other functions used to operate the system. A user interface can have a process graphic display, showing major piping, valves, instrumentation, and system components. The control system can operate in fully automatic modes. However, the system's pumps and valves may be controlled manually if a recipe is inactive. The control system can allow for user-programming of recipes (methods). Recipe operations can be recoverable in the event of a power failure.

The system can be capable of monitoring, at a minimum, the following process parameters: pre-reaction vessel feed pressure; post-reaction vessel pressure, temperature, density, flow rates, total flow; UV absorbance; conductivity; and valve positions.

The system can be capable of generating, at a minimum, alarms under the following conditions: high pressure; flow deviation from setpoint; flow sensor fault; pump fault; E-stop actuation; valve fault; and purge loss; and independent duplex operation.

Alarm logic can be performed in the PLC. For flow and pressure deviation alarms, the code evaluates the process value against low (flow only), low (flow only), high, and high (pressure only) alarm set points. For discrete alarms, the code evaluates if the alarm bit is in an alarm state. One variable table can be used for each process alarm and one for each group status/communication (discrete) alarm. If the process value is in an alarm state, an alarm delay begins counting. When the full delay time expires, the process alarm becomes active. All discrete alarms are scanned once every five seconds, so no delay is used. If, during a scan, a discrete alarm trigger is active, the alarm instantly becomes active.

Interlock logic executes continuously and overrides all automated and manual commands to the interlocked devices. Pumps and valves are not only interlocked by alarms, but also invalid flow paths. If only one pump is used in the flow path, it interlocks the other pump. Then, a port selection is made where the specified amidite/reagent/solvent port is opened, and the desired pump is enabled. Conditional statements are also used to prevent invalid port selections based on the flow path selected. The pumps and valves are also interlocked by high pressure alarms and instrument status or communication failures. If any of these critical alarms occur, the pumps are disabled, a delay occurs, and then all valves are closed.

A dose deviation interlock can analyze dose accuracies for the detrytilation (when using fixed volume), coupling charge, oxy/thio charge, and capping charge steps. If the actual volume delivered varies by more than a defined amount from the recipe target, the system can pause after the proceeding wash has completed.

Valve inputs and outputs are compared, and if any disagreements occur, the system can pause after the proceeding wash has completed. If the alarm is related to a faulty position sensor, this allows the recipe to end at a safe state before troubleshooting the cause.

The system can be capable of collecting run data and displaying stored data and presenting real-time data from process instrumentation on a graphical display, including but not limited to flow transmitters; pressure transmitters; UV absorbance meters; conductivity meters; valve position; and secure login.

The following examples are provided to illustrate a method of synthesizing oligonucleotides using two synthesizer modules capable of independent operation. The modules are operated in sequence wherein a first unit provides a nucleotide to a first reaction vessel at an equivalent excess. The second unit receives a solution output from the first reaction vessel and provides the solution plus an added equivalent of the nucleotide to a second reaction vessel.

EXAMPLES

Two commercially available laboratory synthesizer systems were interconnected effectively in the manner illustrated in FIG. 6 in order to reuse coupling solution(s) from the first synthesizer reaction vessel in an oligonucleotide polymerization on a second reaction vessel. The effect of number of dosing events that a first reaction vessel can be dosed was studied. The amounts studies were a double coupling (0.6 eq+1.0 eq) or a single additive coupling.

Example 1 (Control)

1. Dose 1.3 equivalents of coupling reagent to reaction vessel 1.

Recirculate for 5 min.
After that, wash reaction, reaction vessel 1.

Example 2

1. Dose 0.6 equivalents of coupling reagent to reaction vessel 1.
Recirculate for 5 min (same as usual coupling time).
Do not wash reaction vessel 1.
2. Dose 1.0 equivalents of coupling reagent to reaction vessel 1.
Recirculate for 5 min (same as usual coupling time).
Do not wash reaction vessel until step 3 recirculation has begun.
3. Push "unused" 0.6 equivalent from reaction vessel 1 into reaction vessel 2 using 2.5 reaction vessel volume (CV of acetonitrile (ACN). Recirculate for 5 min (same time used as step #1). Do not wash reaction vessel 2.
4. Dose 1.0 equivalents of coupling reagent to reaction vessel 2.
Recirculate for 5 min (same time used as step #1).
Wash reaction vessel 2 as normal to waste.

Example 3

1. Dose 0.6 equivalents of coupling reagent to reaction vessel 1.
Recirculate for 5 min (same as usual coupling time).
Do not wash reaction vessel 1.
2. Dose 1.0 equivalents of coupling reagent to reaction vessel 1.
Recirculate for 5 min (same as usual coupling time).
Do not wash reaction vessel until step 3 recirculation has begun.
3. Push "unused" 0.6 equivalent from reaction vessel 1 into reaction vessel 2 using 2.5 CV of ACN.
Continue pushing additional 2 CV of ACN for washing transfer tube. Recirculate for
5 min (same time used as step #1). Do not wash reaction vessel 2.
4. Dose 1.0 equivalents of coupling reagent to reaction vessel 2.
Recirculate for 5 min (same time used as step #1).
Wash reaction vessel 2 as normal to waste.

Example 4

1. Dose 1.6 (combined) equivalents of coupling reagent to reaction vessel 1.
Recirculate for 5 min (same as usual coupling time).
Do not wash reaction vessel until step 3 recirculation has begun.
2. Push "unused" 0.6 equivalent from reaction vessel 1 into reaction vessel 2 using 2.5CV of ACN.
Continue pushing additional 2 CV of ACN for washing transfer tube. Recirculate for 5 min (same time used as step #1). Do not wash reaction vessel.
3. Dose 1.0 equivalents of coupling reagent to reaction vessel 2.
Recirculate for 5 min (same time used as step #1).
Wash reaction vessel as normal to waste.

Example 5

1. Dose 1.6 (Combined) equivalents of coupling reagent to reaction vessel 1.
Recirculate for 5 min (same as usual coupling time).

Do not wash reaction vessel until step 3 recirculation has begun.

2. Push "unused" 0.6 equivalent from reaction vessel 1 into reaction vessel 2 using 2.5CV of ACN.

Change the valves for bypass line. Continue pushing additional 2 CV of ACN for washing transfer tube. Recirculate for 3 min. Do not wash reaction vessel.

3. Dose 1.0 equivalents of coupling reagent to reaction vessel 2.

Recirculate for 5 min (same time used as step #1).

Wash reaction vessel as normal to waste.

Figure 7:
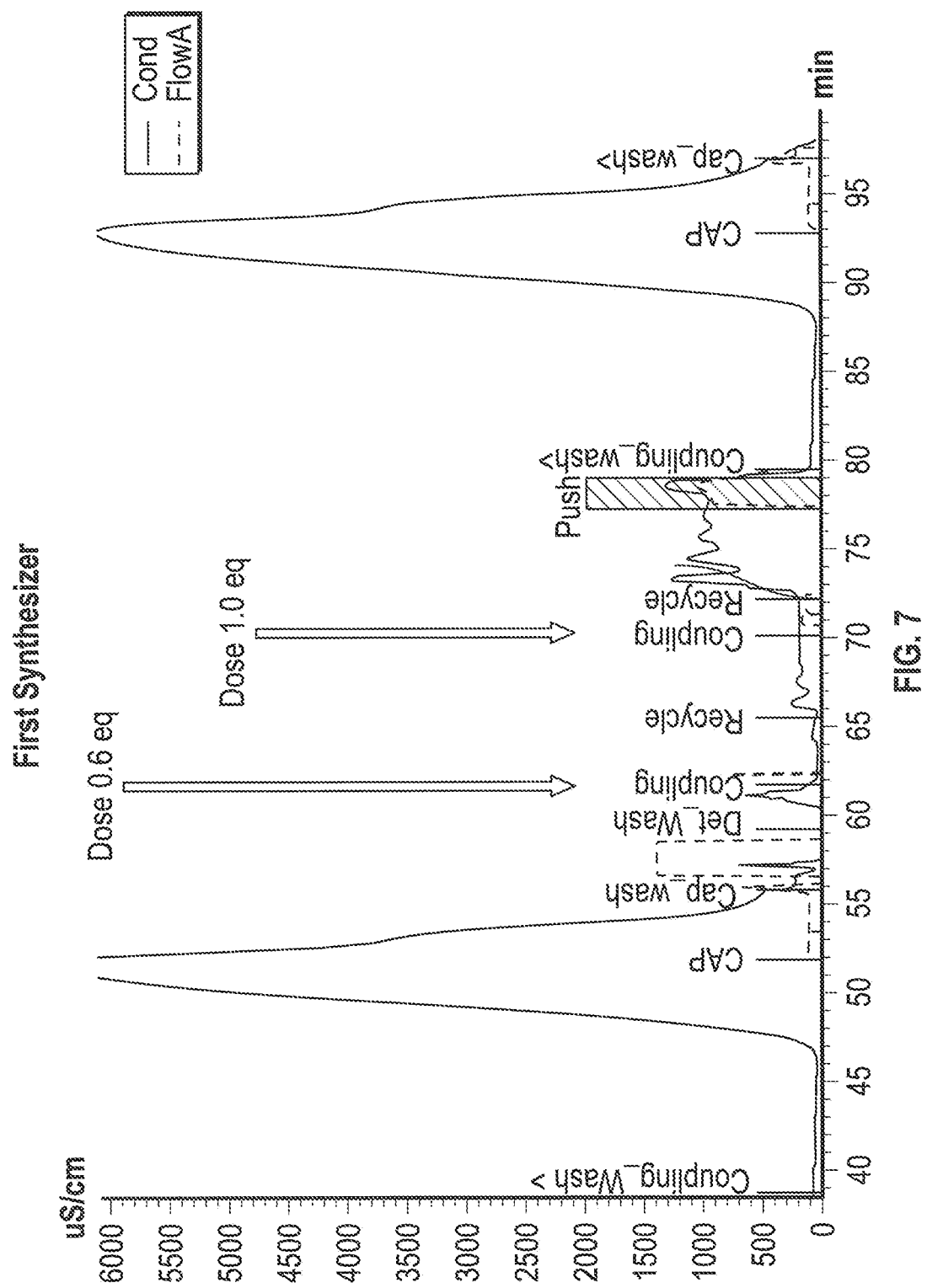
FIG. 7 is a graphical depiction of a coupling liquid introduction sequence by volume over time at a first synthesizer.
Figure 8:
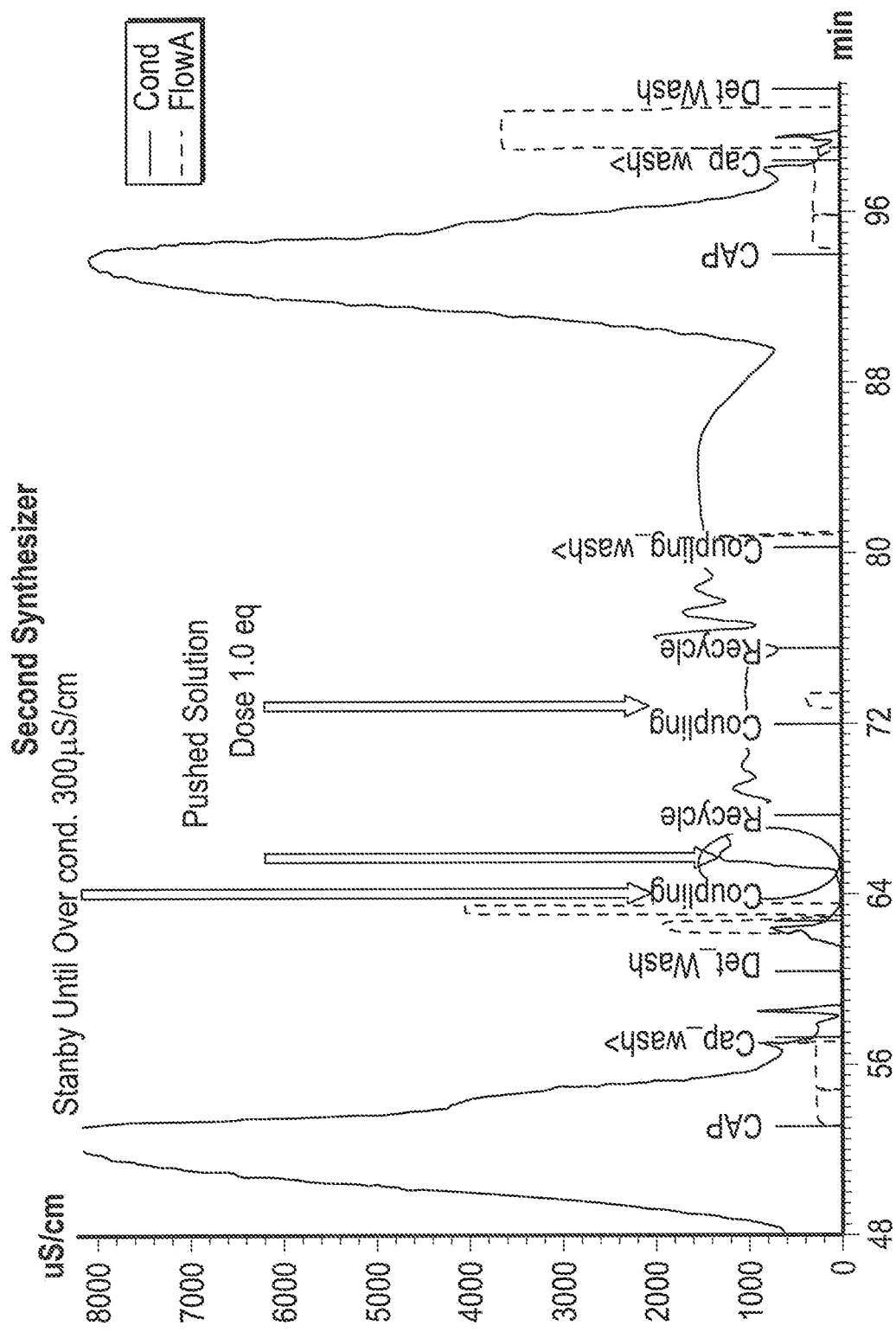
FIG. 8 is a graphical depiction of a coupling liquid introduction sequence by volume over time at a second synthesizer.

FIGS. 7 and 8 visually illustrate the dual synthesizing module process using amidite push.

FIG. 9 demonstrates the Conditions of Coupling for the Examples.

The graph in FIG. 10 shows the comparison of full length product (FLP) obtained for the different experiments. Conditions 2-1 and 2-2 showed insufficient washing inside of the transfer-tube. The FLP of 2-2 was 39.8% due to the residual coupling solution in the transfer-tube. Therefore, the transfer-tube was washed by an additional 2CV ACN. Purity of the second reaction vessel (3-2) was improved to 78.6%. FLP of (5-1) and (5-2) was 84.3% and 80.7%, respectively.

Figure 11:
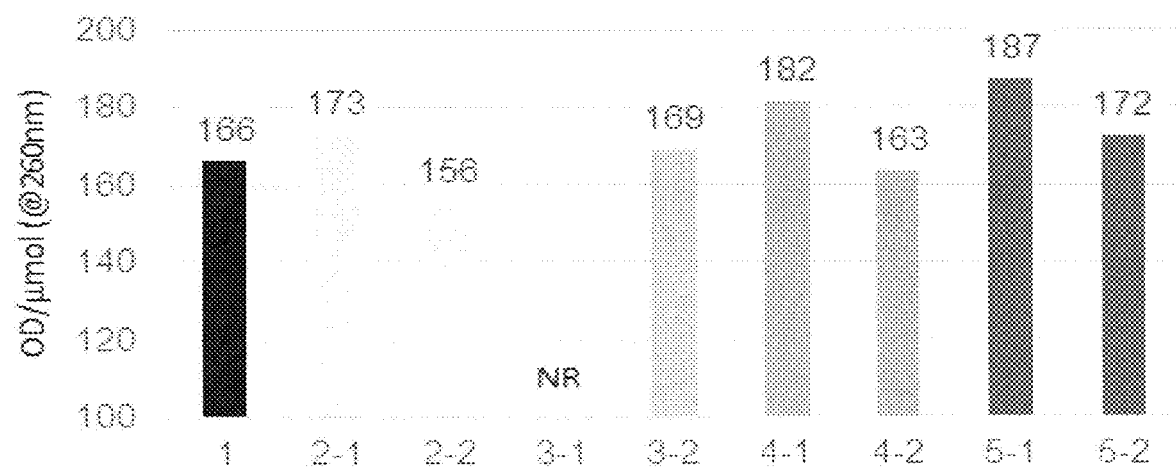
FIG. 11 is a graphical depiction of the optical density (OD) obtained for the Examples.

The graph in FIG. 11 illustrates that the optical density (OD) per μmol were higher for the "pushed" systems (187 and 172) than the control condition (166).

The present disclosure describes an improvement over early systems in oligonucleotide synthesis. This leads to optimization of reaction and wash times, as well as optimization of the quantities of reagents and makes possible economical, commercial-scale production of these increasingly valuable and important complex organic materials yielding optimum quantities of a purer product, at lower cost, and in less time than has heretofore been possible. The system further allows for efficient use of excess.

Although this description has focused on the multi-stage solid-phase synthesis of oligonucleotides, it will be apparent to those skilled in the art that the apparatus and process of this invention have application to the synthesis of other long-chained organic molecules, for example, peptides, polysaccharides, and both RNA- and DNA-based oligomers and analogs thereof such as peptide nucleic acids (PNA) and other mimetics, and may be adapted to such related applications based on routine experimentation. All of such related applications are also considered to be within the scope of this invention.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A system for synthesizing organic polymers comprised of at least two batch synthesizer modules designed for interconnectivity to expand scale range and/or recirculate liquid from a reaction vessel, each module provides liquid monomers and reagents to the fluidly connected reaction vessel, the system comprises:

a first synthesizer module including a plurality of monomer inlet ports, each of the monomer ports associated with a different type of monomer, each monomer port including an inlet valve for receiving the associated monomer, and at least two pumps to provide blending operations, a controllable inlet valving arrangement fluidly coupled to the outlet port of the synthesizer for providing the selected monomer or reagent to the reaction vessel, a controller for controlling the pumps, the blending ratio, and the controllable inlet valving arrangement for either delivery or recirculation of solutions, and valving for fluid interconnection to another synthesizer and/or reaction vessel; and a second synthesizer module in fluid communication with said first synthesizer module, whose controller acts in programmed modes of coordination with said first synthesizer module;

wherein the first and second synthesizer modules feed a common reaction vessel, wherein a controller of the first synthesizer module stores a batch recipe and leads the actions required to perform the synthesis chemistry and the controller of the second synthesizer module acts in a follow mode based on control communication from the controller of the first synthesizer.

2. The system of claim 1, wherein the first and second synthesizer modules feed separate reaction vessels and are run sequentially.

3. The system of claim 1 further including at least a third synthesizer module.

4. The system of claim 1, wherein the pumps comprise gear pumps.

5. The system of claim 1, wherein said valving arrangement is comprised of air activated block diaphragm valves.

6. The system of claim 1, wherein each synthesizer module includes valves in fluid connection with another synthesizer module.

7. The system of claim 1, wherein each pump includes a symmetric fluid path of common length to its respective inlet and outlet connections.

8. A method of synthesizing oligonucleotides comprising at least two synthesizer modules capable of independent operation, said modules being operated in sequence wherein a first module provides a nucleotide to a first reaction vessel at an equivalent excess and said second module receives a solution output from said reaction vessel, and wherein said second module provides said solution output plus added nucleotide to a second reaction vessel or the first reaction vessel at a later position in a sequence being formed.

9. The method of claim 8, wherein an operating system of said first module controls said second module.

10. The method of claim 8, wherein said second synthesizer module further receives one of an ancillary synthesis agent, a coupling agent, and/or a wash solvent from the first reaction vessel.

11. An apparatus for the multi-stage solid-phase synthesis of long-chained organic compounds, said apparatus comprising in combination: (a) a reaction vessel suitable for containing a support/starting material; (b) a plurality of fluid reservoirs; (c) conduits interconnecting each of said fluid reservoirs with said reaction vessel; (d) valves associated respectively with each of said fluid reservoirs, said valves comprising a machined block of stainless steel; (e) gear pumps, wherein said gear pumps number less than ¼ of said valves; and (f) optical scanning means capable of monitoring informed, ultraviolet or visible light of at least two wavelengths for continuously monitoring the chemical composition of effluent from said reaction vessel; the apparatus further comprising a recirculation path including a valve having an inlet from said chamber, an inlet from said fluid reservoirs, an inlet from a gear pump, and an outlet in fluid communication with the gear pump and a waste control valve.

12. The apparatus of claim 11, including a human machine interface allowing operator control of apparatus components.

13. The apparatus of claim 11, wherein said conduits comprise flexible tubing.

14. The apparatus of claim 11, further comprising a plurality of two-way valves blocked together.

15. The apparatus of claim 11, wherein said valves include at least one 3-way block valve and at least one 4-way block valve.

16. The apparatus of claim 11, including at least eight reservoirs and only two pumps.

17. The apparatus of claim 11, wherein at least several of said fluid reservoirs are amidite reservoirs and wherein a flow path from each amidite reservoir to the reaction vessel is at least substantially the same length and volume.

18. The apparatus of claim 11, further comprising an outlet configured for fluid communication with a second apparatus for synthesis.

19. The apparatus of claim 11, wherein said gear pumps magnetically attach to the apparatus.

\* \* \* \* \*